(12) United States Patent
Chang (10) Patent No.: US 7,798,957 B2
(45) Date of Patent: Sep. 21, 2010

(54) COLONOSCOPE GUIDE AND METHOD OF USE FOR IMPROVED COLONOSCOPY

(76) Inventor: Stanley F. Chang, 2723 W. Tenaya Way, Fresno, CA (US) 93711

( * ) Notice: Subject to any disclaimer, the term of this patent is extended or adjusted under 35 U.S.C. 154(b) by 159 days.

(21) Appl. No.: 11/496,375

(22) Filed: Jul. 31, 2006

(65) Prior Publication Data
US 2008/0027281 A1 Jan. 31, 2008

(51) Int. Cl.
*A61B 1/04* (2006.01)
*A61B 1/00* (2006.01)
*A61M 1/00* (2006.01)

(52) U.S. Cl. ................. 600/114; 600/144; 604/27

(58) Field of Classification Search ............ 600/114, 600/121, 128, 131, 137, 144, 138; 604/109, 604/165.04, 27
See application file for complete search history.

(56) References Cited

U.S. PATENT DOCUMENTS

| | | | |
|---|---|---|---|
| 5,280,781 A | 1/1994 | Oku | |
| 5,337,733 A | 8/1994 | Bauerfeind et al. | |
| 5,370,109 A | 12/1994 | Cuny | |
| 5,386,818 A | 2/1995 | Schneebaum et al. | |
| 5,779,624 A | 7/1998 | Chang | |
| 5,941,815 A * | 8/1999 | Chang | 600/114 |
| 6,503,192 B1 | 1/2003 | Ouchi | |
| 6,712,755 B2 | 3/2004 | Chang | |
| 6,790,173 B2 | 9/2004 | Saadat et al. | |
| 6,793,621 B2 * | 9/2004 | Butler et al. | 600/114 |
| 6,800,056 B2 * | 10/2004 | Tartaglia et al. | 600/114 |
| 6,837,846 B2 | 1/2005 | Jaffe et al. | |
| 6,855,107 B2 | 2/2005 | Avni et al. | |
| 6,960,162 B2 | 11/2005 | Saadat et al. | |
| 6,960,163 B2 | 11/2005 | Ewers et al. | |
| 6,974,411 B2 | 12/2005 | Belson | |
| 6,984,203 B2 | 1/2006 | Tartaglia et al. | |
| 2003/0233066 A1 * | 12/2003 | Ewers et al. | 604/27 |
| 2004/0044350 A1 * | 3/2004 | Martin et al. | 606/139 |

OTHER PUBLICATIONS

Cotton, P.B. & Williams, C.B., "Practical Gastrointestinal Endoscopy," 1996, pp. 217-220, Fourth Edition, Blackwell Science Ltd., US.

* cited by examiner

*Primary Examiner*—Linda C Dvorak
*Assistant Examiner*—Alireza Nia
(74) *Attorney, Agent, or Firm*—Richard A. Ryan (57) ABSTRACT

A guide and method for tilting a colonoscope in the rectum during a colonoscopy to attain a favorable direction for advancement of the scope through the colon. The guide comprises an at least partially rigid, elongated body member that, preferably, is attached to a handle at its proximal end. The body member can have a flat or curved cross-section. One or more ring members can be provided along the length of the body member to receive the scope and maintain the guide in close abutting relation therewith. The ring members can be slotted to allow side-loading of the guide onto the scope. Alternatively, a rigid or graduated rigid tubular member can be part of the guide member. An injection port allows injection of a lubricant. By tilting the colonoscope at various difficult stages of a colonoscopy, sigmoid looping is minimized to facilitate advancing the scope through the colon.

31 Claims, 8 Drawing Sheets

COLONOSCOPE GUIDE AND METHOD OF USE FOR IMPROVED COLONOSCOPY

BACKGROUND OF THE INVENTION

1. Field of the Invention

The field of the present invention relates generally to devices and procedures for use in endoscopic examinations of the human colon. More specifically, the device and method of the present invention relates to medical equipment and procedures used to overcome the difficulties encountered with looping of the sigmoid during a colonoscopy. Even more specifically, this invention relates to guiding devices and methods of their use which facilitate the insertion of the endoscope into and through the human colon by tilting the endoscope to prevent or overcome problems with sigmoid looping.

2. Background

As used herein, the term "endoscope" or "scope" is used to refer to a endoscope, colonoscope, sigmoidoscope, proctoscope or other types of medical endoscopes. As known to those skilled in the art, a typical endoscope generally comprises a connecting tube, a handle and an insertion tube (the part inserted into the patient). In the text, the term "scope" generally refers to the insertion tube portion of the endoscope. In referring to the opposite ends of the scope or the guide of the present invention, the "proximal end" refers to that part of the scope or guide which is closest to the operator or physician endoscopist (hereinafter collectively referred to as "operator") performing the procedure, and the "distal end" refers to that part of the scope or guide farthest from the operator or physician endoscopist. Although medically the rectum is generally not considered to be part of the colon, which includes the sigmoid colon, descending colon, transverse colon and ascending colon, for purposes of this disclosure general references herein to the term "colon" include the rectum. The terms "splint", "splinting device", and "overtube" are used interchangeably to refer to a generally elongated hollow tubular member that is adaptable for receiving a medical instrument, such as an endoscope, therein to facilitate movement of the scope through the colon.

Colonoscopy is the most sensitive and specific means for examining the colon, particularly for the diagnosis of colon cancers and polyps. Because the cecum, the portion of the colon farthest from the anus, can be a common location for cancer, it is generally desirable that the entire colon be completely examined. During a typical colonoscopy procedure, the scope is inserted into the anus, through the rectum, and then advanced through the sigmoid colon, descending colon, transverse colon, ascending colon and into the cecum. In colonoscopy, straightness of the endoscope is necessary, or at least highly desirable, for the advancement of the endoscope through the colon. Advancing the scope, which is typically about 160 centimeters in length, can be difficult due to a loop in the sigmoid colon. In fact, the advancement of the scope during the colonoscopy procedure often results in the formation of a loop along the shaft of the flexible scope. This looping occurs most commonly in the sigmoid colon and, though usually much less frequently, in the transverse colon. As known to those skilled in the art, failure to substantially straighten the loop in the sigmoid colon prior to continuing to advance the scope can cause enlargement of the loop and result in even more difficulty in advancing the scope. This enlarged looping can result in patient pain and damage, including cardiovascular reactions such as hypotension and bradycardia. Forceful pushing of the scope in the colon when loops are present only increases the pain and is usually ineffective in advancing the scope through the colon. Pain increases the need for sedative and analgesic medications, which can expose the patient to more cardiorespiratory risk.

To address the issue of looping in a colonoscopy, the operator typically utilizes a series of maneuvers, referred to herein as the usual colonoscopic maneuvers, that can be summarized as pushing, pulling, rotating (clockwise or counterclockwise), jiggling, inflation, deflation (suction), external abdominal compression and changing the patient's position, which are done in various combinations and/or sequences as necessary or desirable. The scope is inserted into the rectum and gradually advanced with the usual colonoscopic maneuvers through the sigmoid. In a typical colonoscopy, the sigmoid loop is formed as the scope moves inward. The operator will reduce and then straighten the sigmoid loop by withdrawing the scope to a generally straightened position after he or she reaches the descending colon or the transverse colon. Once the loop is substantially straightened, further advancement of the endoscope can usually be accomplished. Unfortunately, it is not uncommon that upon readvancement of the scope, the sigmoid loop has a tendency to reform. The operator will attempt to prevent or limit reformation of the sigmoid loop with abdominal compression and by changing the position of the patient, thereby allowing advancement of the scope to the cecum. As well known, however, the usual colonoscopic maneuvers are ineffective in a certain number of cases. In fact, subsequent reformation of the sigmoid loop is the most troublesome impediment to the advancement of the distal tip of the scope and accounts for many, if not most, of the failures to reach the cecum, which typically results in three to ten percent of colonoscopies.

The variable stiffness colonoscopes, such as the Innoflex™ video colonoscope available from Olympus America, Inc., is somewhat helpful in dealing with the problem of sigmoid looping during colonoscopy. The use of a sigmoid splint or overtube has also been found to be highly effective in preventing reformation of the sigmoid loop in order to facilitate advancement of the scope through the colon during a colonoscopy. The prior art sigmoid splinting overtubes are all inserted over a straightened scope through the rectum and sigmoid into the descending colon to passively form a bridge between the anus and the descending colon so as to facilitate further scope advancement. These overtubes are all fairly flexible in order to be safely inserted into the descending colon and none of them are of graduated rigidity. As such, the prior art overtubes are not capable of actively tilting the axis of the scope in the rectum, which is the objective of the present invention. Furthermore, the method of using a short overtube, sufficiently rigid, to actively tilt a flexible endoscope in the rectum, has never been disclosed.

As is well known, splints are not easy to use and can cause complications such as perforation. In addition, when the need for a sigmoid splint arises, the tip of the scope is usually already in the proximal colon. At this point, the operator may opt to remove the scope entirely in order to load the endoscope inside the sigmoid splint, in an end-to-end fashion, and start the procedure over again. A more convenient way, however, is to be able to load the endoscope into the splint without having to remove the scope from the patient. This is done by using a splint with a longitudinal slot along the length of the splint. The slotted splint is loaded onto the endoscope in a side-to-side fashion by opening the slot, such that the scope does not have to be removed from the patient. Once placed around the scope, the slot is closed. The slot will then need to be fastened or locked in the closed position. A fastening or locking mechanism is needed to keep the splint closed in a secure fashion. There are many patents that teach the use of overtubes/splints for colonoscopy, including U.S. Pat. No. 5,779,624, U.S. Pat. No. 5,941,815 and U.S. Pat. No. 6,712,755, all to Chang (the present inventor).

In addition to variable stiffness scopes and the use of splints, the old-fashioned rigid proctoscope/sigmoidoscope has existed for decades. These rigid scopes are used for the purpose of examining the rectum and part of the sigmoid. When in the rectum, they have to be angled in various directions, often quite severely, to gain optimal views. The fact that these devices have been in use for many years shows that tilting a round, cylinder-shaped instrument in the rectum is safe. However, these rigid proctoscopes/sigmoidoscopes directly tilt the rectum. They do not tilt flexible endoscopes and have never been designed or designated for facilitating the advancement of a flexible endoscope through the colon.

A video proctoscope is described in "Practical Gastrointestinal Endoscopy", by Peter Cotton and Christopher Williams, 4th edition, p. 219. A proctoscope is first inserted into the distal rectum. The insertion trocar is removed. A flexible colonoscope is next inserted into the proctoscope. The colonoscope provides a source of illumination and an excellent close-up view of the distal rectum and anus, especially of hemorrhoids. This combination is used to gain a good view of the distal rectum, but not to facilitate colonoscopy. Specifically, no mention is made in this text of using the proctoscope to tilt the path of the colonoscope. Furthermore, the short proctoscope shown in the illustration (FIG. 9.22) is insufficient in length to tilt the colonoscope at or near the rectum-sigmoid junction in order to facilitate colonoscopy.

Despite the prevalence of specially configured endoscopes and splints to reduce sigmoid looping in order to improve the effectiveness and reduce the pain of colonoscopy procedures, many operators still face significant difficulty and, on occasion, are unable to reach the cecum due to looping of the sigmoid. As a result, therefore, what is needed is a device and a method of using that device that improves the use of an endoscope during a colonoscopy by reducing the problems associated with insertion and advancement of the scope through the colon. The improved device and method should simplify the colonoscopy procedure and reduce the operator labor and patient discomfort presently associated with colonoscopies that result from sigmoid looping. Preferably, the device should be relatively inexpensive to manufacture, easy to use and adaptable for use at various stages of the colonoscopy.

SUMMARY OF THE INVENTION

The colonoscope guide and method of use for improved colonoscopy of the present invention provides the benefits and solves the problems identified above. The colonoscope guide, also interchangeably referred to herein as a "guide" or "vector guide" device, and method of the present invention are based on the anatomical consideration that pushing an unaided flexible endoscope through the rectum moves the scope forward in the craniocaudal axis and on the geometrical consideration that pushing a flexible endoscope in the craniocaudal axis tends to cause looping of the sigmoid. The guide is configured for tilting the scope in a generally oblique direction in the rectum, typically toward the left side of the patient, so as to reduce the difficulty of inserting and advancing the scope in and through the colon. The guide of the present invention simplifies the performance of a colonoscopy by directing the scope into the colon in a manner that reduces sigmoid looping and generally prevents reformation of the loop during the procedure. The method of the present invention moves the direction of scope insertion away from the craniocaudal axis into an oblique axis, to at least approximately align the rectum with the descending colon. Various embodiments are disclosed to enable this active tilting of the scope in the rectum toward the descending colon. As such, the guide of the present invention reduces operator labor to perform the colonoscopy and reduces the pain and discomfort of the patient that would otherwise result from sigmoid looping. In its preferred embodiment, the guide of the present invention is relatively inexpensive to manufacture and adaptable for use when the scope is inserted into the anus and/or during later advancement of the scope through the colon. The method of the present invention, utilizing the above-referenced device, is relatively simple to follow and effective at improving the likelihood of reaching the cecum while reducing patient discomfort and pain.

In one embodiment of the present invention, the colonoscope guide comprises an elongated body member that can be configured to be generally flat, curved or semi-circular having an inner side that abuts against the colonoscope inside the rectum and sigmoid colon. The curved and semi-circular cross-section configurations provide improved engagement with the scope. Further improved engagement is achieved with a wider distal end, a more semicircular shape cross-section and/or the use of one or more ring members or a tubular member to receive the scope and hold the guide in generally abutting relation therewith. A handle is provided at the proximal end of the body member to allow the operator to manipulate the guide so as to direct and maintain the angle of the scope to improve the ability to advance it through the colon by reducing the sigmoid loop and preventing its reformation. The guide can be provided with an injection port hydraulically connected to one or more channels having one or more discharge openings to allow the operator to inject lubricant along the inner surface to improve the guide sliding along the scope or the scope sliding along the guide.

To perform a colonoscopy procedure using an endoscope and the guide configured according to an embodiment of the present invention, the operator introduces the scope into the colon and advances it as far as possible using usual colonoscopic maneuvers. Once the operator is no longer able to advance the scope or advance it without causing pain, he or she pulls back on the scope until the sigmoid loop is essentially reduced and then inserts the guide into the rectum on the patient's right side of the scope. Using the anus as a fulcrum point, the operator tilts the guide to the patient's left side to push the scope in that direction so as to better align the rectum and sigmoid colon with the descending colon. With the scope tilted to substantially straighten the colon, the operator then continues with the colonoscopy by advancing the scope through the colon. In an alternative method of use, the guide, most likely in the form of an overtube or partial overtube, can be first introduced into the rectum. The scope is next inserted or engaged with the guide. The guide and scope are advanced together, while tilting of the guide and manipulation of the scope are carried out. To pass through the sigmoid colon, the guide is tilted toward the descending colon and, preferably, the scope is maintained in that tilted axis while advancing.

In summary, the method of the present invention is to utilize a device to actively tilt a flexible endoscope in the rectum toward the descending colon to help minimize the formation or reformation of a sigmoid loop in the performance of a colonoscopy. This method has not been previously disclosed.

Accordingly, the primary objective of the present invention is to provide a colonoscope guide and method of use for improved colonoscopy that provides the advantages and features discussed above and which overcomes the disadvantages and limitations associated with presently available devices for and methods of performing colonoscopy procedures.

It is also an important objective of the present invention to provide a colonoscope guide and method of its use that reduces the difficulties associated with performing a colonoscopy which are due to sigmoid looping.

It is also an important objective of the present invention to provide a colonoscope guide and method of its use that simplifies insertion and advancement of an endoscope through a colon having sigmoid looping that reduces operator labor and time to perform the colonoscopy and which reduces patient discomfort and pain associated with such procedures.

It is also an important objective of the present invention to provide a colonoscope guide that is configured to effectively and safely tilt or angle the colonoscope and maintain it in that direction so as to ease its insertion into and advancement through the colon, particularly in light of sigmoid looping that is present in the colon.

It is also an important objective of the present invention to provide a method of performing a colonoscopy that utilizes a colonoscope guide to substantially reduce the effect of sigmoid looping in order to ease the insertion and advancement of the endoscope into and through the colon.

It is also an important objective of the present invention to provide a colonoscope guide having a generally elongated body, preferably with a handle at its proximal end, that is adapted to tilt or angle an endoscope as it enters and advances through the colon during a colonoscopy.

The above and other objectives of the present invention are explained in greater detail by reference to the attached figures and description of the preferred embodiment which follows. As set forth herein, the present invention resides in the novel features of form, construction, mode of operation and combination of parts presently described and understood by the claims.

BRIEF DESCRIPTION OF THE DRAWINGS

In the drawings which illustrate the best modes presently contemplated for carrying out the present invention.

DETAILED DESCRIPTION OF THE PREFERRED EMBODIMENTS

With reference to the figures where like elements have been given like numerical designations to facilitate the reader's understanding of the present invention, the preferred embodiments of the present invention are set forth below. The enclosed figures and drawings are merely illustrative of a preferred embodiment and represent one of several different ways of configuring the present invention. Although specific components, materials, configurations and uses are illustrated, it should be understood that a number of variations to the components and to the configuration of those components described herein and in the accompanying figures can be made without changing the scope and function of the invention set forth herein.

Figure 2:
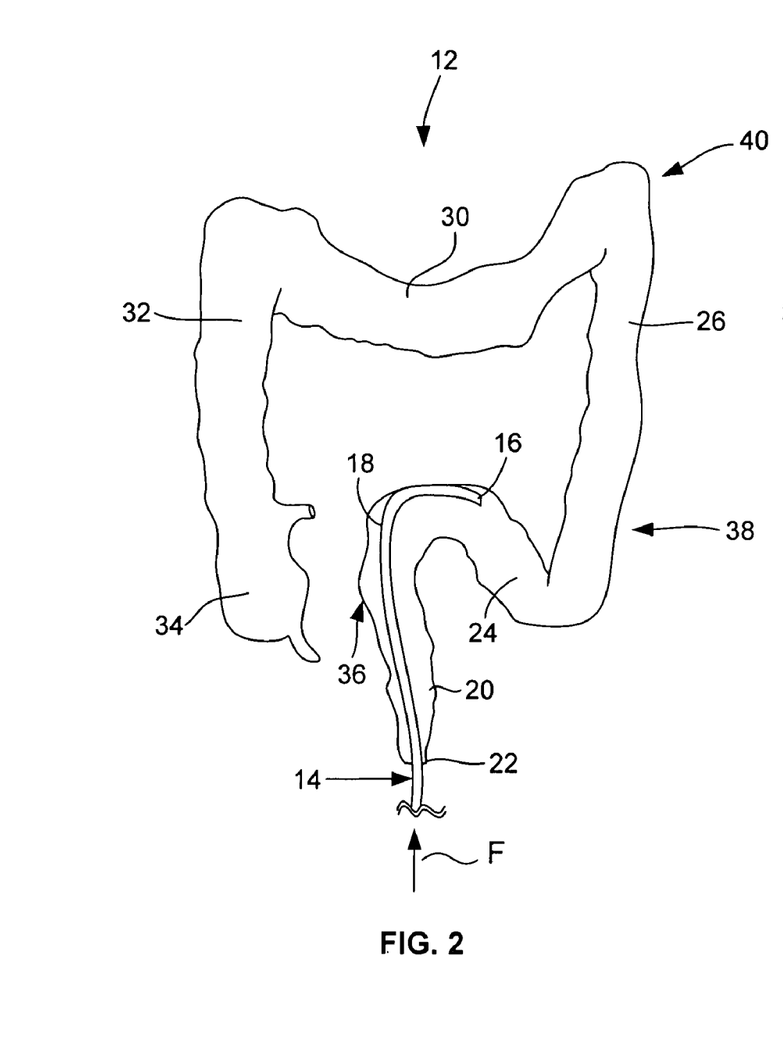
FIG. 2 illustrates a scope advancing into the sigmoid before use of the guide of the present invention.
Figure 3:
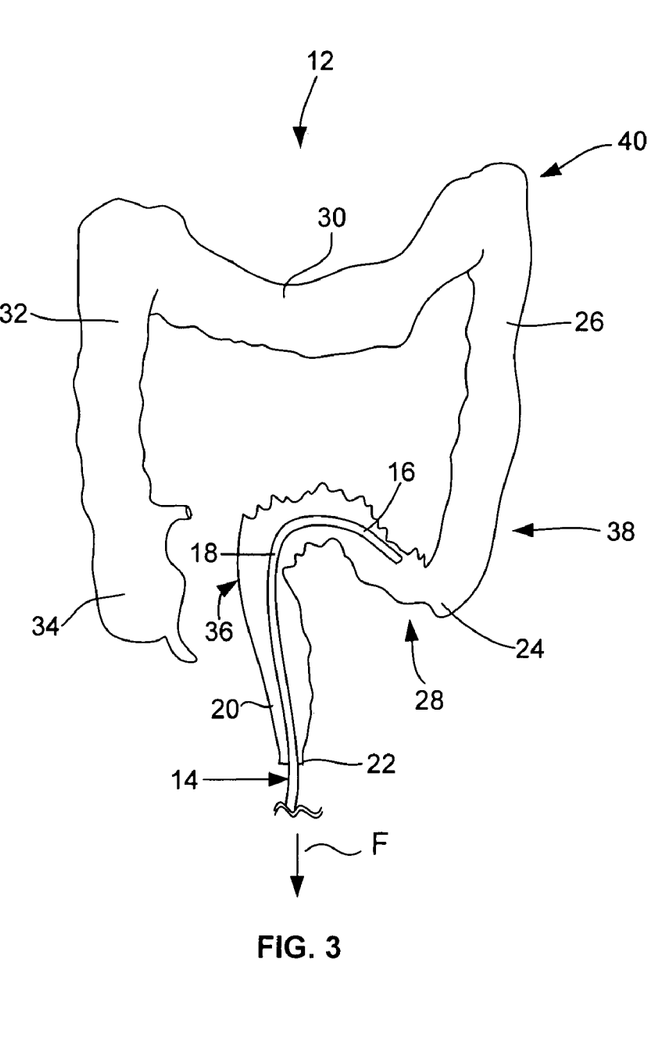
FIG. 3 illustrates the scope from FIG. 2 reaching the proximal sigmoid after pushing, pulling, rotating and etc. with the usual colonoscopic maneuvers in the sigmoid to pleat and shorten it, as shown by the accordioned contour of the sigmoid.
Figure 9:
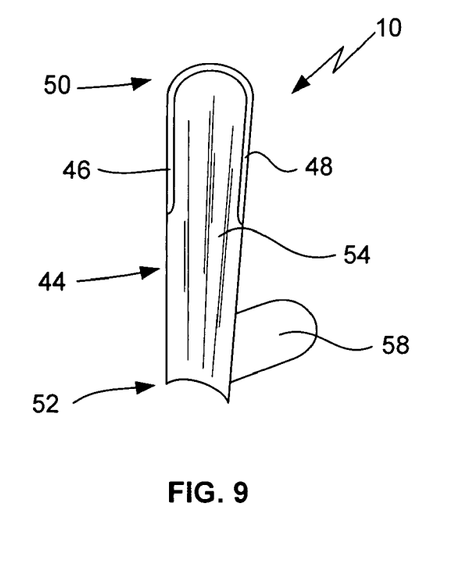
FIG. 9 is a side view illustrating one of the preferred embodiments of the colonoscope guide of the present invention showing the body member being wider and having a curved cross-section at the distal end.
Figure 10:
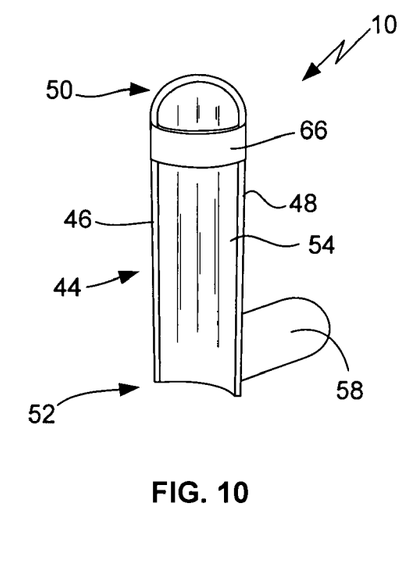
FIG. 10 is a side view illustrating an alternative embodiment of the colonoscope guide of the present invention showing use of a ring member near its distal end.
Figure 11:
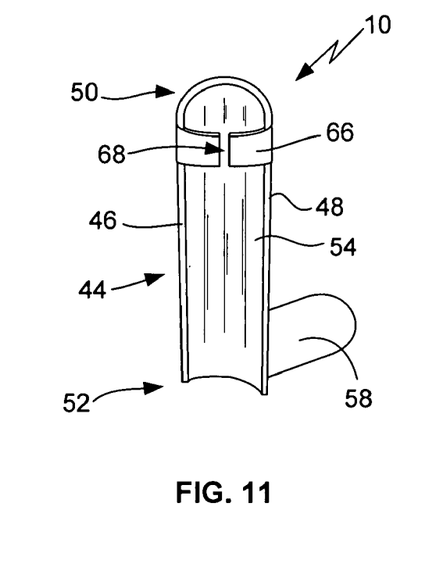
FIG. 11 is a side view illustrating an alternative embodiment of the colonoscope guide of the present invention showing use of a slotted ring member near its distal end.

A colonoscope guide that is manufactured out of the components and configured pursuant to a preferred embodiment of the present invention is shown generally as 10 in the figures, particularly FIGS. 9 through 11. As set forth in more detail below, guide 10 is utilized to assist in the investigation of the colon 12, shown in its entirety in FIGS. 2 and 3, with a colonoscope 14 or equivalent medical device. The distal end or tip 16 and insertion tube or body 18 of colonoscope 14 are introduced into the rectum 20 through the anus 22 and then into the sigmoid colon 24 (with the arrows "F" on the figures showing the movement of the colonoscope 14 into or out of the colon 12). After negotiating the loop in the sigmoid colon 24, the colonoscope 14 enters the descending colon 26. Further advancement of the tip 16 through the colon 12 is made easier by partially withdrawing the colonoscope 14 to straighten the sigmoid colon 24 with the insertion tube 18 of colonoscope 14, causing the sigmoid colon 24 to take on the accordioned contour 28 (as shown in FIG. 3). Once the sigmoid colon 24 is generally straightened, the tip 16 of the colonoscope 14 is advanced to the descending colon 26, through the transverse colon 30 and ascending colon 32 and then into the cecum 34. After withdrawal of colonoscope 14 and completing the colonoscopy procedure, the colonoscope 14 is removed from the patient.

Figure 4:
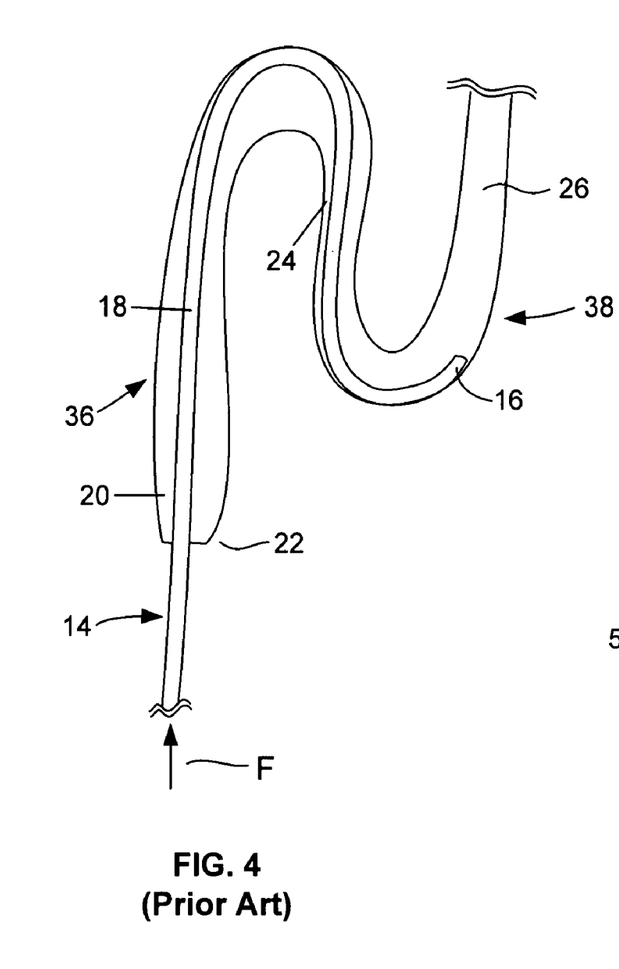
FIG. 4 is a prior art configuration illustrating the scope from FIG. 3 forming a loop in the sigmoid because the force of pushing is directed generally cephalad or nearly cephalad.
Figures 5, 6:
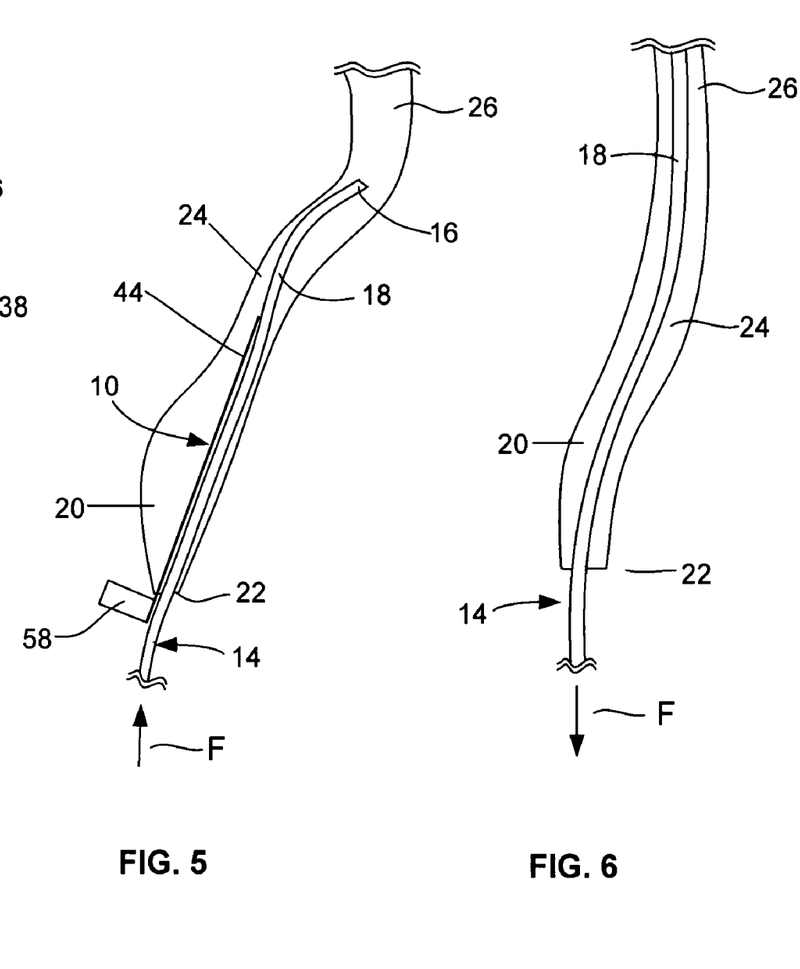
FIG. 5 illustrates the use of the guide of the present invention to tilt the axis of FIG. 3 to the left side of the patient's body to align the rectum toward the descending colon to allow the operator to advance the scope more easily through the colon while avoiding formation of the sigmoid loop.
FIG. 6 illustrates the scope in the proximal descending colon, with the scope pulled back to generally straighten it (a gentle "S" shape remains)
Figure 7:
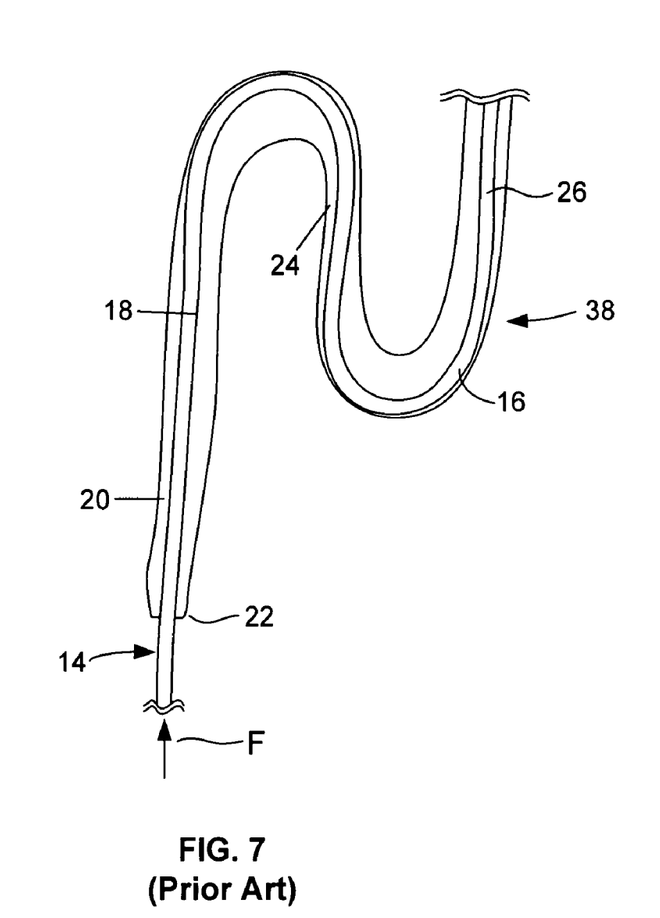
FIG. 7 illustrates the prior art pushing of the scope from FIG. 6 with a loop resulting because the force of pushing is directed cephalad or nearly cephalad.

The typical problems that arise in colonoscopy are best shown in FIGS. 4 and 7. At one or more points (shown in FIGS. 2 and 3) during scope 14 advancement through the sigmoid 24, the lumen of the proximal sigmoid 24 and/or the descending colon 26 is clearly and invitingly in view in front of the scope tip 16. However, typically, pushing scope 14 in the prior art fashion (i.e., in the cephalad direction) will not directly move the tip 16 into this lumen. Instead, a loop forms in the sigmoid 24, shown in FIG. 4, before the tip 16 moves forward. This scenario is extremely familiar to all colonoscopists (i.e., the lumen ahead is "so close, yet so far"). Later in the colonoscopy procedure, with tip 16 of scope 14 further upstream and after pulling back to straighten (i.e., as shown in FIG. 6), the prior art cephalad pushing of the scope 14 causes the sigmoid 24 to loop again (shown in FIG. 7). Typically, in the prior art, pushing the scope 14 causes the tip 16 to not move or even move backwards. This is an extremely common scenario in colonoscopy. The reformation of the sigmoid loop can occur repeatedly en route to the cecum 34. The movement of the scope 14 from FIG. 3 to the loop of FIG. 4 and from FIG. 6 to the loop of FIG. 7 is where the patient incurs pain. As explained more in detail below, use of guide 10 of the present invention is intended to eliminate or substantially eliminate the loops of FIG. 4 and 7, such that the colonoscopy proceeds from that shown in FIG. 3 to the condition shown in FIG. 5, skipping the loop of FIG. 4, and from that shown in FIG. 6 to the condition shown in FIG. 8, skipping the loop of FIG. 7.

Figure 1:
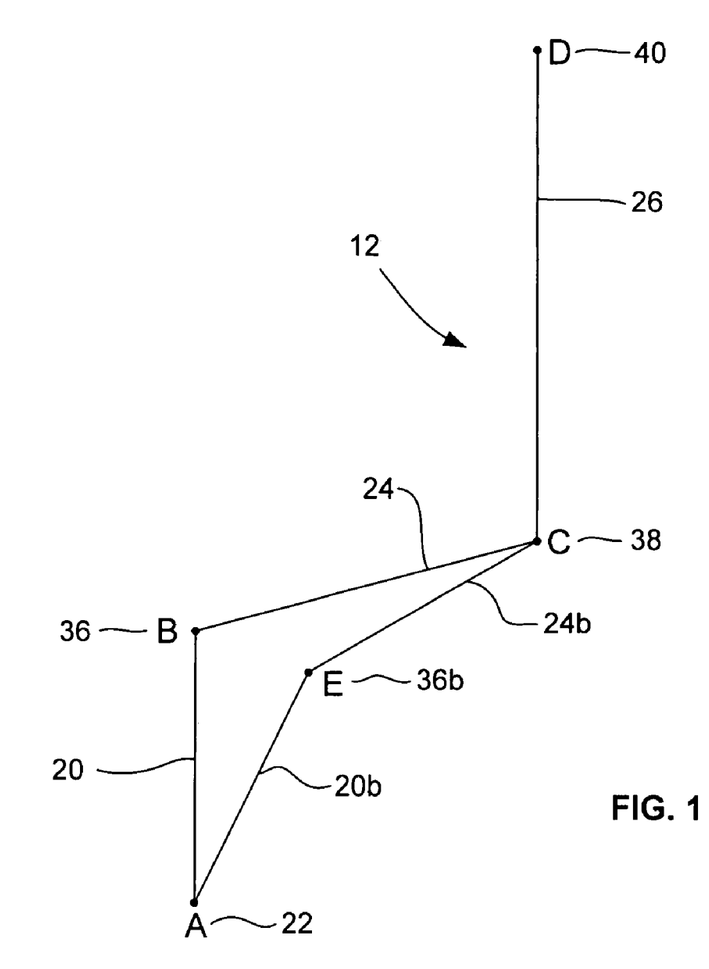
FIG. 1 is a schematic diagram representing the geometry of a section of the colon, with the segment AB representing the rectum in its natural craniocaudad axis, segment BC representing the sigmoid, segment CD representing the descending colon and segments AE and EC representing the axis change resulting from use of the guide of the present invention.

The guide 10 and method of the present invention offers a solution for the problem of sigmoid looping, the looping best shown in FIGS. 4 and 7, in colonoscopy. The cause of sigmoid looping, from the anatomical and geometrical perspective, is that the force of pushing the scope 14 during a typical or prior art colonoscopy is generally limited to the craniocaudal axis (references to the craniocaudal herein are intended to refer to both craniocaudal and nearly craniocaudal). The cephalad direction of push predisposes the colon 12 to sigmoid looping, while the desirable direction of the force is obliquely toward the descending colon 26. The solution presented by the guide 10 and method of the present invention is to tilt and maintain the scope 14 in the rectum 20 more leftward, referencing the left side of the patient's body from the patient's perspective, to allow the force of pushing the scope 14 to be generally directed toward the descending colon 24. This objective is shown in the schematic of FIG. 1, with point A representing the anus 22, line segment AB representing the rectum 20, line segment BC representing the sigmoid colon 24, point B representing the recto-sigmoid junction 36, line segment CD representing the descending colon 26, point C representing the sigmoid-descending junction 38 and point D representing the splenic flexure 40 during a typical or prior art colonoscopy. When a colonoscopy is performed with the guide 10 of the present invention, point E in FIG. 1 illustrates the positioning of the recto-sigmoid junction 36b, or vicinity, after the guide 10 improves the alignment of the rectum and sigmoid colon, shown as 20b and 24b respectively after being acted upon by guide 10, with the descending colon 26 to improve the colonoscopy procedure (as set forth in more detail below).

As well known to those skilled in the art, the rectum 20 is a hollow tubular organ situated at about midline in the craniocaudal orientation. Viewed laterally, it is posterior in position and curves gently anteriorly along the sacrum as it meets the sigmoid 24. It is mostly extraperitoneal, attached by ligaments and fascia, to maintain its craniocaudad orientation. After reaching the descending or transverse colon, by pulling and straightening scope 14, the rectum 20 can be tilted laterally to generally follow the axis of the descending colon 26, but pushing on the insertion tube 18 of scope 14 tends to move the axis of scope 14 in the rectum 20 back to the craniocaudal orientation (whether just one wall of the rectum 20 is tilted by tilting scope 14 or the rectum 20 as a whole is tilted is inconsequential for purposes of this invention). At about 15 cm above the anus 22, the rectum 20 enters the peritoneal cavity, and then shortly thereafter, it meets the sigmoid 24. It is generally irrelevant, for practical purposes, to regard this intraperitoneal segment of the rectum 20 as the rectum 20 or sigmoid 24, but for purposes of this disclosure, the point where the rectum 20 enters the peritoneum is regarded as the recto-sigmoid junction 36, because the rectum 20 becomes a much less mobile organ below that point. The sigmoid colon 24 is extremely variable in length and shape and it connects the top of the rectum 20 to the lower end of the descending colon 26. From the top of the rectum 20, the sigmoid colon 24 heads leftward (or initially rightward and then leftward), anteriorly and then posteriorly, and generally upward, to join the descending colon 26. The sigmoid-descending junction 38 is highly variable in location. The descending colon 26 is mostly retroperitoneal situated longitudinally and has variable lengths of mesentery and thus mobility. The descending colon 26 is generally oriented craniocaudad, roughly parallel to the rectum 20, and separated from the rectum 20 by about half of the width of the abdominal cavity. The recto-sigmoid junction is usually positioned below the sigmoid-descending junction 38, as best shown in FIGS. 2 and 3.

It is generally well known that the rectum 20 can be safely tilted to one side or another by a stiff or rigid instrument, such as the proctoscope or sigmoidoscope, which is often tilted quite severely in order to obtain a good view of the interior of the rectum 20. During the typical prior art colonoscopy, the rectum 20 is tilted to the left when the colonoscope 14 is pulled back and straightened after reaching the descending colon 26 in order to generally align the rectum 20 with the descending colon 26. A sigmoid splint or overtube, when used, keeps the axis from the anus 22 to the mid-to-proximal descending colon 26 a generally straight line in order to avoid sigmoid loop reformation. Unlike the rigid proctoscope/sigmoidoscope, however, a flexible colonoscope 14, which is necessary to achieve advancement through the descending 26, transverse 30 and ascending 32 colons to reach the cecum 34, is not able to effectively tilt the rectum 20. As a result, the pushing force imparted onto a colonoscope 14, shown by the arrows on FIGS. 2 and 4, is directed generally cephalad and usually cannot go obliquely toward the descending colon 26 on its own.

The cause of sigmoid looping can be simply but adequately explained on the basis of geometry and, although colonic anatomy is three-dimensional, the concept can be illustrated in the two-dimensional schematic of FIG. 1. When a colonoscope 14 is introduced into the rectum 20, it first heads cephalad for about 15 cm in the rectum 20, before entering the sigmoid colon 24. The first 10 cm (approximately) of entry into the sigmoid 24 is accomplished by bending the front four-way bending section of the colonoscope 14, as shown in FIG. 2. However, the direction of movement of the insertion tube 18 is generally limited to the craniocaudal axis, as dictated by the anus 22 and rectum 20, causing a loop to be formed, as best shown in FIGS. 2 and 4. The size and complexity of the loop in the sigmoid 24 can be lessened by skillful application of the ususal colonoscopic maneuvers discussed above, especially with pulling back, rotation and etc., resulting in pleating (shortening) of the sigmoid 24 into the accordioned contour 28 shown in FIG. 3. The configuration of FIG. 3 is usually obtainable even with long, tortuous sigmoids. Subsequent advancement of the scope 14 into the descending colon 26, again by pushing cephalad as dictated by the anus 22 and rectum 20, often reforms the sigmoid loop, as shown in FIG. 4. Looping on initial insertion through the sigmoid 24 can thus occur more than once during the colonoscopy.

Geometrically, the looping of the sigmoid 24 happens because the craniocaudal axis has practically no lateral component. Thus, lateral movement to get through the sigmoid 24, by pushing craniocaudal, depends on deflecting against a loop in the sigmoid 24. The expertise possessed by many operators, especially by using frequent pull-backs and rotations, enables them to reach the descending colon 26 quickly. However, most operators cannot escape the limitations dictated by the unfavorable geometry of the distal colon 12. Conversely, if the scope 14 can be tilted in the rectum 20 to generate an oblique vector, a lateral component is generated. The tilt itself will "nudge" the scope 14 slightly forward laterally. In addition, the force of further pushing along this oblique axis will also go partly laterally, and will also approach the wall of the sigmoid 24 with a more favorable angle, as shown by FIG. 5. In so doing, passage through the sigmoid 24 is accomplished, partly with the direct force of pushing and partly with wall deflection, against a much less tense wall. Sigmoid looping is thus minimized or avoided.

Figure 12:
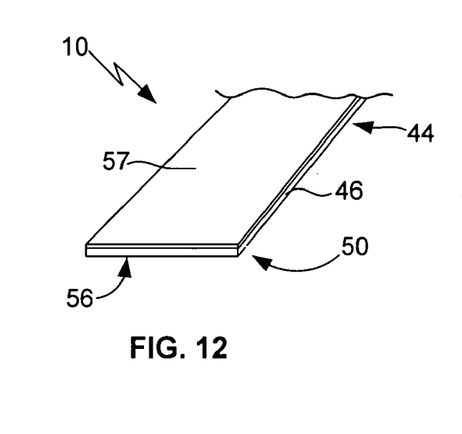
FIG. 12 is a perspective view of the distal end of a colonoscope guide having a generally flat cross-section and provided with a liner material on its inner surface.
Figure 13:
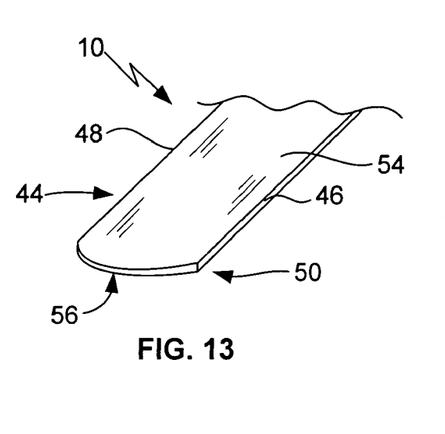
FIG. 13 is a perspective view of the distal end of a colonoscope guide having a generally crescent shaped cross-section.

The guide 10 of the present invention provides a tool for tilting the scope 14 in an oblique direction in the rectum 20, generally toward the left side of the patient. As explained in more detail below, the guide 10 applies external force to the scope 14 inside the rectum 10 to better direct the scope 24 into the descending colon 26 and maintain the scope 14 in that tilted axis. In a preferred embodiment, guide 10 comprises an elongated body member 44, which is sized and configured to be received in rectum 20 through anus 22. Body member 44 can be straight or slightly curved. If curved, body member 44 preferably has a gentle concavity facing the scope 14 during use. A gentle curve can also be provided to accommodate the curvature of the scope 14 in the rectum 20 along the curvature of the sacrum. In one embodiment, shown in FIG. 12, body member 44 is generally flat or planar in cross-section, having first edge 46 and second edge 48 and relatively thin. In a preferred embodiment, however, at least a portion of body member 44 towards its distal end 50 has a non-planar or curved cross-section with non-planar edges 46 and 48, such as the generally crescent shape shown in FIG. 13 or the half-circle shape shown in FIG. 14, to better maintain contact with the scope 14 when inside the colon 12. In addition, the portion of body member 44 towards its distal end 50 can be made generally wider (i.e., from first edge 46 to second edge 48) in cross-section than the portion of body member 44 at its proximal end 52, as shown in FIG. 9, to further assist with partial enclosure of the scope 14. As set forth in more detail below, to facilitate use of guide 10, body member 44 should be made out of generally stiff material that provides a semi-rigid to rigid guide body member 44 to allow the operator to apply a directing force against scope 14, as described herein, and yet still be able to safely and effectively insert the body member 44 into the colon 12 as far as desired. Body member 44 can be made out of metal or a hard plastic material.

If desired, the inner side 54 of body member 44, that being the side which contacts scope 14 during use and opposite outer side 56, can be made or provided with a relatively soft interface, for instance being lined with a liner material 57 made up of a generally softer material such as rubber or the like, so as to prevent scraping against scope 14 during use of guide 10 (e.g., when body member 44 is made out of metal). In addition, the inner side 54, or the liner material 57 lining it, can be coated with a lubricant. A preferred lubricant is a hydrophilic substance, similar to that used to line glide-type guide wires. Hydrophilic substances have the unique property of becoming extremely slippery when wet with water or saline. An adequate layer of the hydrophilic substance should be coated and/or impregnated onto the surface of inner side 54, or its lining, of body member 44. Water or saline is applied to this surface to make the sliding surface extremely slippery, thereby allowing easy passage of the guide 10 along scope 14 or scope 14 along guide 10.

Figure 20:
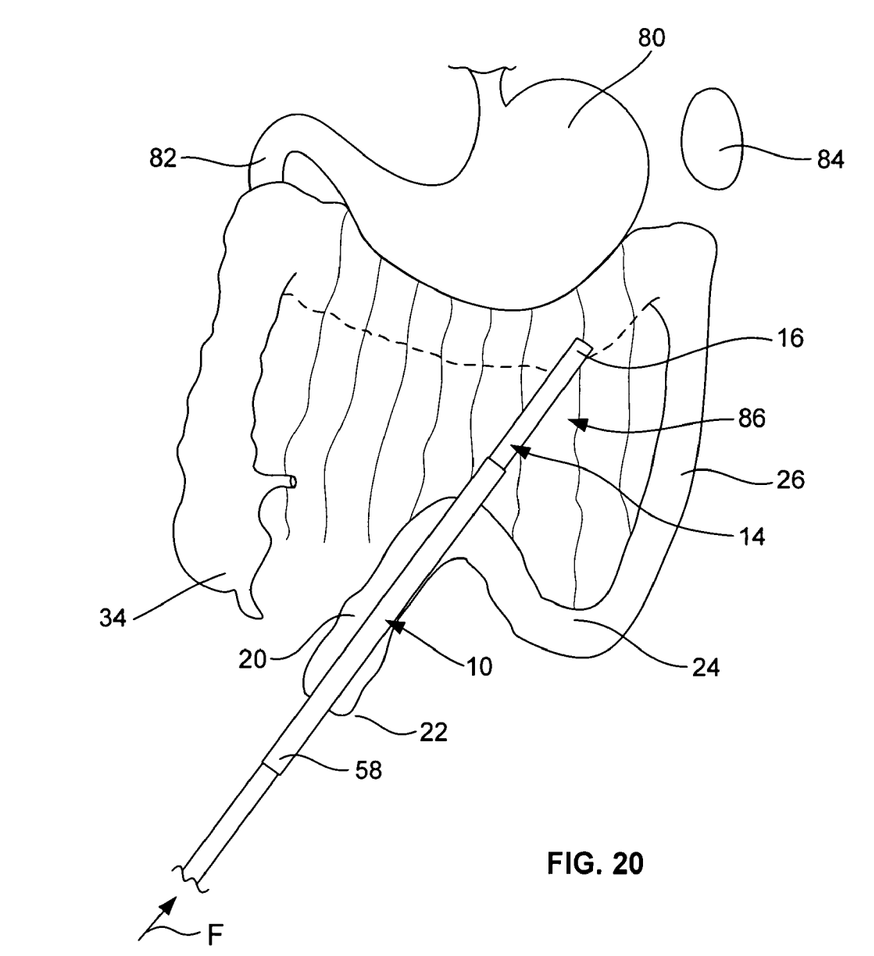
FIG. 20 illustrates use of the guide configured according to a tubular embodiment of the present invention being utilized in a natural orifice transluminal endoscopic surgery procedure to perform a splenectomy.

To facilitate use of guide 10, the proximal end 52 of body member 44 is provided with a handle 58, shown in FIGS. 9-11 and 15-19, which can be attached to or integral with body member 44. Preferably, handle 58 is oriented at an angle to the longitudinal axis of body member 44 and it is sized and configured to prevent full entry of guide 10 into the rectum 20, such as having a larger cross-section (i.e., diameter) than body member 44. Handle 58 should be sized and configured so as to be suitable for grasping by the operator's hand, preferably comfortably, to allow him or her to insert, withdraw, rotate, tilt, and un-tilt body member 44. As is readily apparent from the discussion below, movement of handle 58 controls the direction and degree of tilting of guide 10. When tilting is performed during use of guide 10, the handle 58 tilts the elongated body member 44 of the guide 10 by using the anus 22 as the fulcrum. The elongated body member 44 then tilts or pushes the scope 10 into better alignment with the descending colon 26 so as to reduce looping in sigmoid 24. Preferably, handle 58 is oriented at a suitable angle to the body member 44, including being in continuity with it (as shown in FIG. 20), so the operator can know which direction he or she is pushing the scope 14 while body member 44 is inside the colon 12 during the colonoscopy.

Figure 14:
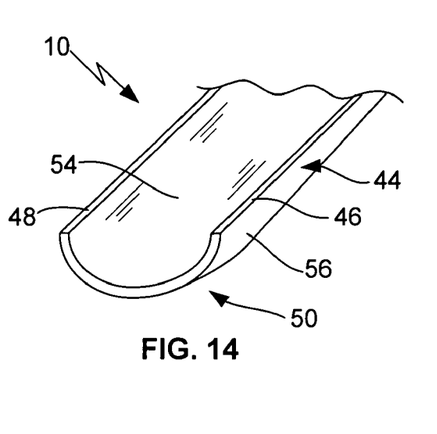
FIG. 14 is a perspective view of the distal end of a colonoscope guide having a generally semi-circular cross-section.
Figure 15:
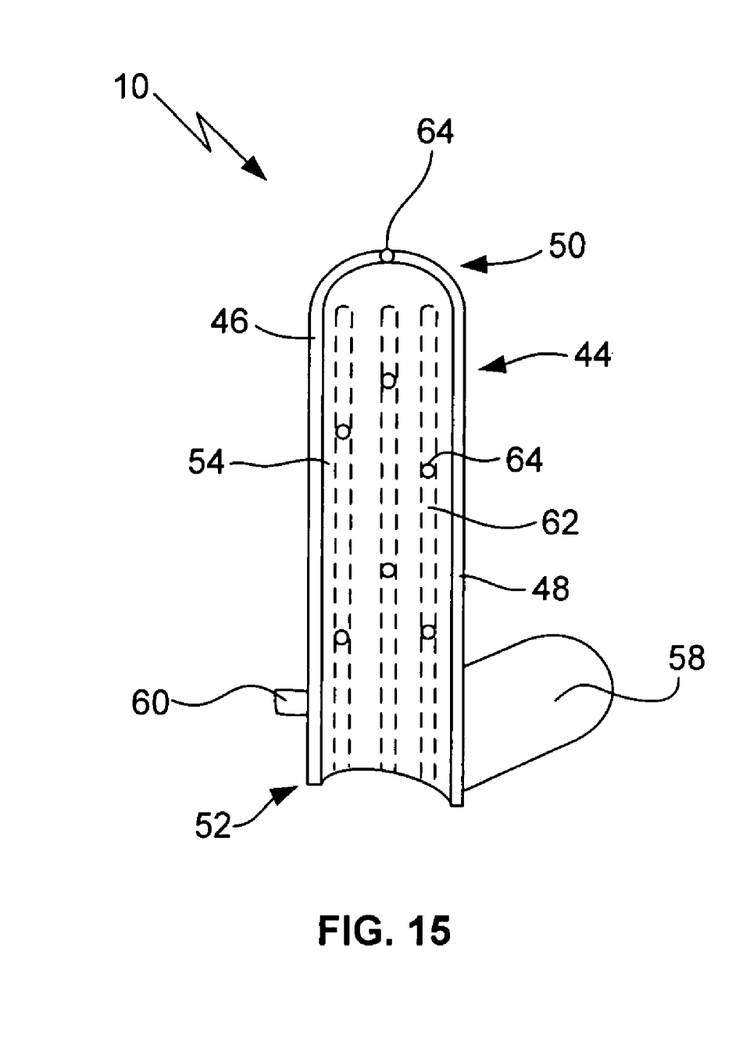
FIG. 15 is a side view illustrating an alternative embodiment of the colonoscope guide of the present invention showing use of an injection port at the proximal end of the body member hydraulically connected to channels having discharge ports on the inner side of the body member.
Figure 16:
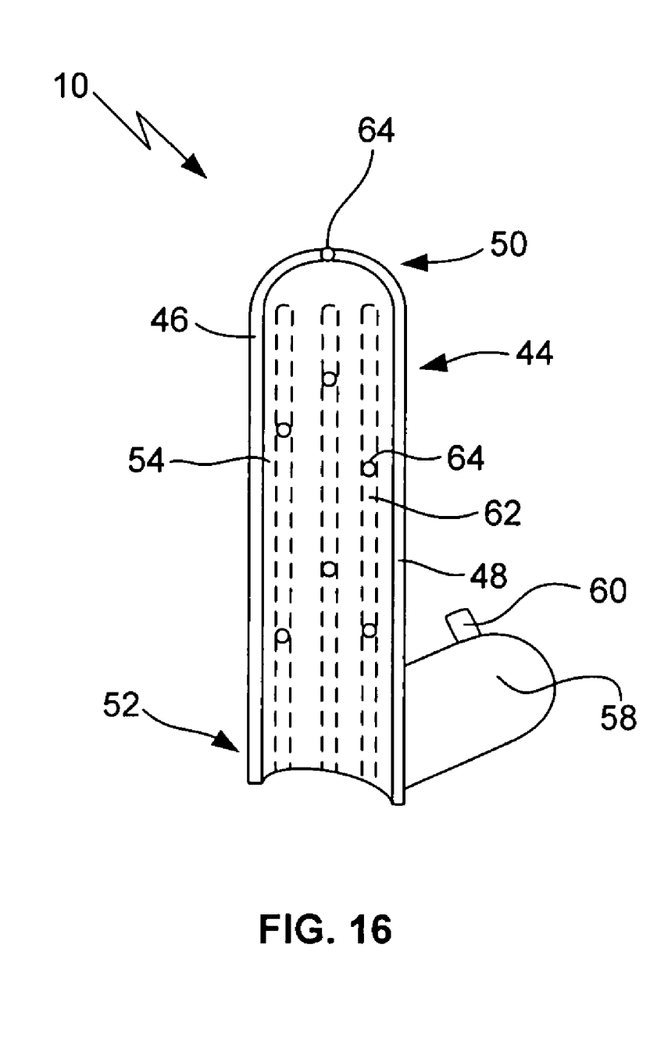
FIG. 16 is a side vide of the embodiment of FIG. 14 with the injection port on the handle.

In an alternative embodiment, shown in FIGS. 15 and 16, guide 10 includes an injection port 60 hydraulically connected to one or more channels 62 disposed inside or along body member 44. Preferably, injection port 60 is configured to connect to or receive a syringe or like device for the injection of lubricant, water, saline solution or other fluid. Each of the channels 62 have one or more discharge openings 64 on inner side 54 for discharging fluid received into channels 62 from injection port 60. In a preferred embodiment, each channel 62 includes a plurality of discharge openings 64 along the longitudinal length of body member 44 and at or near its distal end 50 to discharge fluid, such as a lubricant, onto scope 14 to ease the movement of guide 10 along scope 14 or scope 14 along guide 10. Preferably, the channels 62 are built into body member 44 so as to not be damaged during use or be damaging to the scope. As shown in FIG. 14, injection port 60 can be located at or near the proximal end 52 of body member 44. Alternatively, as shown in FIG. 16, injection port 60 can be placed on handle 58, which may provide some benefits as to the accessibility to injection port 60. If injection port 60 is located on handle 58, a handle channel, tube or like means, shown as 65 in FIG. 16, will have to be provided to hydraulically interconnect injection port 60 with channels 62 to discharge fluid out discharge openings 64. In the preferred embodiment, injection port 60 is adapted to connect to a syringe or other device for receiving fluid into channels 62. If inner side 54, or its lining, is coated with a hydrophilic lubricant, injection port 60 can be utilized to inject water or other fluid to enhance the lubricity of guide 10. Discharge openings 64 can all be the same size or be different sizes. Preferably, the size of discharge openings 64 is selected to allow the fluid injected into channels 62 to be distributed generally evenly along the inner side 54 of body member 44.

At one or more locations along the length of guide 10, particularly at its distal end 50 as shown in FIGS. 10 and 11, one or more ring members 66 can be incorporated into (i.e., integral with) or attached to body member 44 to substantially encircle the scope 14 during use for a colonoscopy. The ring members 66 are provided to ensure the guide 10 follows the scope 14 as it moves in the colon 12 and facilitates the pushing, pulling, and various lateral tilts that the guide 10 may impart to the scope 14. In a preferred embodiment, ring members 66 have a generally circular cross-section to encircle the scope 14 with an inner diameter only slightly larger than the outer diameter of the scope 14. Also in the preferred embodiment, ring member 66 has a longitudinally disposed slot 68, as shown in FIG. 11, along the length of ring member 66 to facilitate loading the guide 10 onto scope 14 when the scope 14 is already inside the colon 12. In use, the slot 68 is opened to receive the scope 14 inside ring member 66 in a side-loading configuration. The slot 68 is closed, with scope 14 inside ring member 66, by utilizing one or more commonly known closure mechanisms (not shown), such as adhesive tape that is wrapped around body member 44 at ring member 66. Another example of a closure mechanism is shown in U.S. Pat. No. 6,712,755 to Chang, which is incorporated herein by this reference. If ring member 66 is not provided with slot 68, then guide 10 must be preloaded onto the scope prior to its insertion into the colon 12. If desired, the ring members 66 can be coated with a hydrophilic substance or other lubricant to enhance the sliding of the scope 14 inside the ring members 66 and help prevent pinching of the mucosa of the colon 12. Additionally, the ring members 66 can be made out of a soft material in order to not scrape the scope 14 and be made collapsible to facilitate exchanging the scope 14 during the colonoscopy, as described below.

Figure 17:
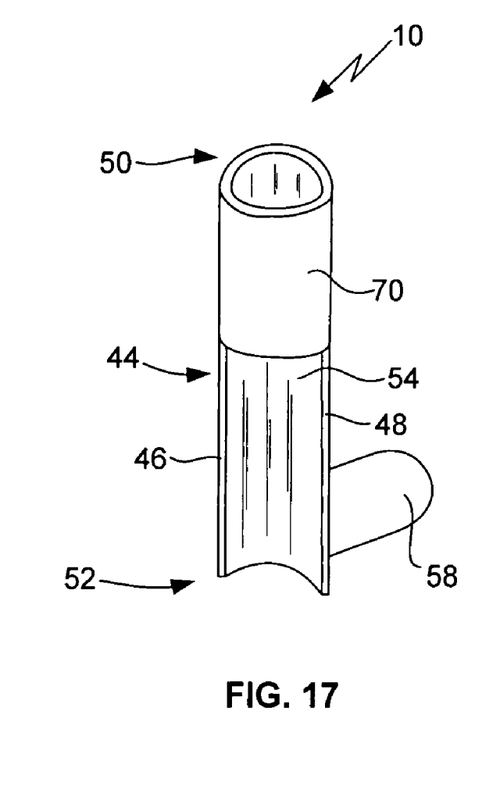
FIG. 17 is a side perspective view of a guide configured according to an alternative embodiment of the present invention showing use of a tubular member at the distal end of the body member.
Figure 18:
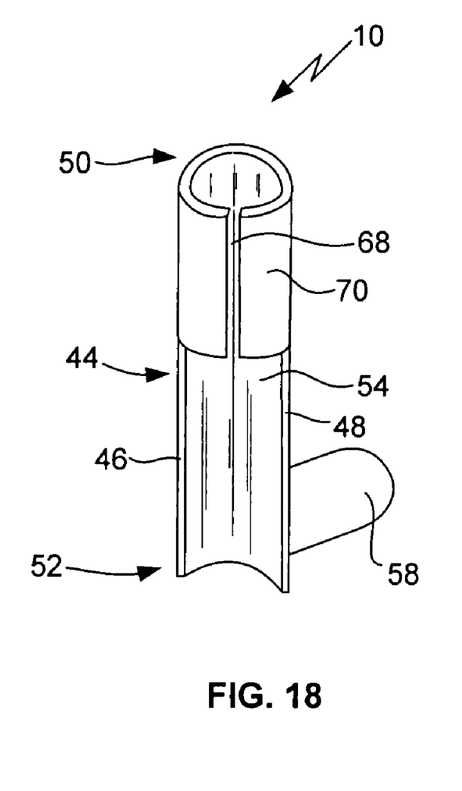
FIG. 18 is a side perspective view of a guide configured according to an alternative embodiment of the present invention showing use of a slotted tubular member at the distal end of the body member.
Figure 19:
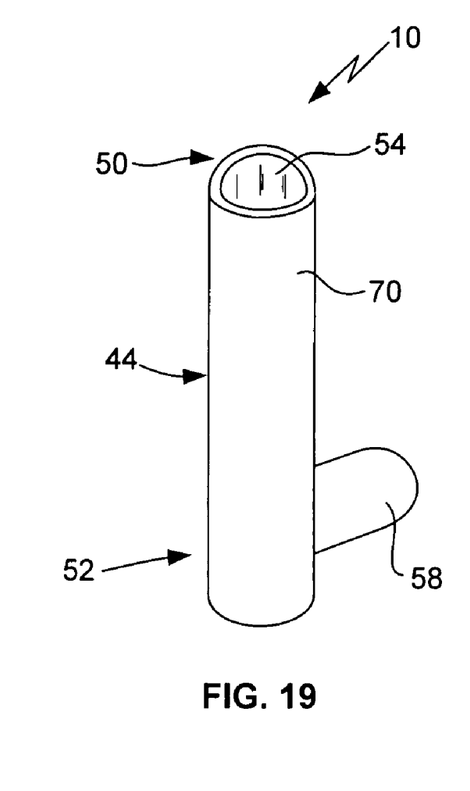
FIG. 19 is a side perspective view of a guide configured according to an alternative embodiment of the present invention showing use of a tubular member that extends the entire length of the body member.

As an alternative to or in conjunction with the use of ring members 66, guide 10 can be provided with a short tube member 70, as shown in FIGS. 17 and 18, that is integral with or attached to body member 44 such that it resembles and functions similar to a short overtube/splint. In the preferred configuration of this embodiment, tube member 70 is an at least partially rigid tube that is placed at or near the distal end 50 of body member 44. In an alternative embodiment, shown in FIG. 19, tube member 70 can extend a substantial part or even all of the length of body member 44, essentially providing an overtube as guide 10. Preferably, the distal end 50 of body member 44 of this embodiment would include a distal seal or sealing mechanism as described in U.S. Pat. No. 5,779,625 (which is incorporated herein by this reference), so as to reduce or prevent perforation of colon 12. In use, the guide 10 having a non-slotted tube 70 (FIG. 17) is preloaded onto scope 14 by inserting scope 14 through tube member 70 and then sliding the guide 10 generally towards the proximal end (not shown) of scope 14 before beginning the colonoscopy. When the guide 10 is needed, the operator slides guide 10 distally to enter the rectum over the scope 14. If tube 70 is provided with a longitudinally disposed slot 68, such as shown in FIG. 18, then the need to preload guide 10 onto scope 14 is eliminated. As discussed above, a closure mechanism will be necessary to close slot 68 after loading scope 14 in tube 70.

Generally, it is preferred that the length of body member 44 be approximately 10 to 20 cm, which is approximately the same length as rectum 20. In another embodiment, particularly when utilized for the exchange of scopes 14, the length of body member 44 can be 20 to 70 cm. It will be generally preferred that guide 10 having a shorter length body member 44, will have body member 44 that is made out of materials and configured to provide a generally rigid body member 44 to better facilitate directing the scope 14 in the rectum 20. Guides 10 having longer body members 44 will generally need to be made out of materials which are or which provide a less rigid body member 44 to allow body member 44 to generally flex according to the contours of scope 14 in colon 12, yet be sufficiently stiff to bend the scope 14 as needed or desired. In another embodiment, guide 10 will have a body member 44 that is of graduated stiffness, with body member 44 being more rigid towards its proximal end 52 and less rigid (or more flexible) towards its distal end 50 to provide both the greater ability to tilt in and near the rectum 20 and to generally flex in the descending colon 26 and transverse colon 30. In the embodiment where the cross-section is curved (i.e, the crescent or half circle embodiments shown in FIGS. 13 and 14, respectively), the width of body member 44 is preferably provided with, at least at its distal end 50, an inner surface 54 that is only slightly larger than the width of scope 14. As will be readily apparent to those skilled in the art, guide 10 can have a variety of different configurations and width to accomplish the objectives set forth herein and accomplish the method of use set forth below. If desired, more than one of such configurations can be utilized during a colonoscopy procedure.

Use of colonoscope guide 10 of the present invention can be initiated at either the beginning of the colonoscopy or upon reformation of a loop in the sigmoid 24 later in the procedure. During the initial introduction of the scope 14 through the sigmoid 24, with the lumen of the sigmoid 24 or descending colon 26 clearly seen straight ahead (which typically occurs when the tip 16 of the scope 14 is at the sigmoid-descending junction 38, looking ahead into the descending colon 26), the scope 14 is pulled back as much as possible. At this stage, the operator recognizes that further advancement of the scope 14 will require and depend upon formation of a substantial and/or painful sigmoid loop, despite the use of usual colonoscopic maneuvers. The solution is to use the guide 10 to tilt the scope 14 in the rectum 20 to the left and maintain the tilt, with adjustments in the angle, while pushing the scope 14 forward. The scope 14 will then advance without the painful sigmoid loop. In a preferred embodiment, this is accomplished by pulling the scope 14 as far back as possible without losing positioning inside the colon (to the extent possible), while keeping the lumen of the sigmoid 24 and/or descending colon 26 in view. The guide 10 is then introduced into the rectum 20 along the scope 14, and gently tilted leftward while lubricant or other fluid is injected by the assistant. The lumen of sigmoid colon 24 or descending colon 26 is constantly kept in view by adjusting the bending section of the scope 14, while at the same time gently pushing the scope 14 to advance it into the lumen while lubricant is injected through injection port 60. In doing so and by minimizing loop formation, the sigmoid 24 will be found to be very short, and the descending colon 26 will be reached quickly and with relatively little pain. If a loop is felt to form, the scope 14 can be pulled back again, and then the steps of tilting the guide 10 with lubricant injection, tip adjustment and pushing are repeated as necessary or desirable.

A common situation arises when the tip 16 is in the distal descending colon 26, looking straight ahead at the lumen of the descending colon 26, and yet pushing only causes a painful loop to form in the sigmoid 24. The guide 10 can be easily used to tilt the scope 14 in the rectum 20 leftward to be more in line with the descending colon 26, and then pushing the scope 14 will result in an efficient and painless advancement of the scope 14 into the descending colon 26. In using this technique, there is no need to form an alpha loop, a maneuver to try to "soften" the angle of insertion of the scope 14 into the sigmoid 24 to lessen pain. While usual colonoscopic maneuvers remain important, looping of the sigmoid 24 can be mitigated by the use of the guide 10 of the present invention. Thus, in addition to being an improved substitute for the sigmoid splint/overtube device, the guide 10 can also help in the initial insertion of the scope 14 through the sigmoid 24.

Figure 8:
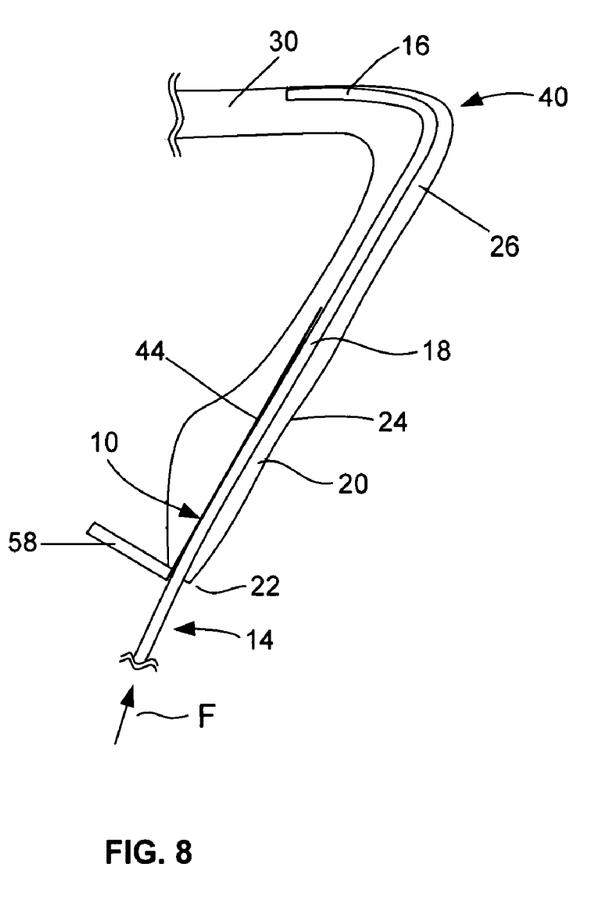
FIG. 8 illustrates the guide of the present invention being used with FIG. 6 to tilt the scope so as to generally line up with the descending colon, the axis from the anus to the descending colon being relatively straight and being maintained by the guide of the present invention pushing against the scope as it is efficiently advanced.

In the scenario where the scope 14 is already advanced to the descending colon or beyond when a loop in the sigmoid 24 forms, the scope 14 is pulled back to undo the sigmoid loop, before further advancement. As known to those skilled in the art, at certain point or points during the colonoscopy when the scope 14 in the descending 26, transverse 30 or ascending 32 colon, pushing causes the scope 14 to "buckle" in the sigmoid 24, and the tip 16 fails to advance or even moves backward. This feeling is very familiar to all colonoscopists or other operators. It can be quite a struggle, with even the usual colonoscopic maneuvers being ineffective. The sigmoid loop can reform when pushing the scope 14 against increased frictional resistance. The hepatic flexure is especially problematic as it is suspected that at that point, much of the lubricant at the distal aspect of the scope 14 has been deleted by contact with the colon wall. When such resistance occurs, pushing the scope 14 causes the rectum 20, slightly tilted by straightening the scope 14, to go back to its craniocaudal axis. Further pushing of the scope 14 thus sets off the same chain of events. With the scope 14 pulled back to straighten again, the scope 14 in the rectum 20 can again be readily tilted leftward by using the guide 10. With the scope 14 held in this oblique axis, the force of pushing will now go directly in line with the descending colon 26, and the forward force for scope 14 advancement is transmitted much more effectively to its tip 16, as shown in FIG. 8.

Thus, as set forth above, the vector guide 10 can be used multiple times throughout a colonoscopy procedure. The guide 10 can be used on initial insertion and then again and again subsequently. As the procedure becomes much quicker, easier, and more predictable, cecal intubation rate also increases, while pain, and its associated consequences, are lessened.

In summary, the craniocaudal axis of the pushing force causes sigmoid looping. By tilting the axis of scope 14 during insertion, looping can be minimized through the sigmoid 24. Later into the procedure, sigmoid looping can also be avoided using this same method, as the scope 14 in the rectum 20 is kept in line with the descending colon 26. As stated above, from the configuration of FIG. 3, the prior art colonoscopy usually goes to FIG. 4, a very painful move for the patient. Using the guide 10 and method of the present invention, however, the procedure would go to FIG. 5 instead, which is far more desirable for the patient than FIG. 4. Similarly, from FIG. 6 the prior art colonoscopy may go to FIG. 7, whereas utilizing the guide 10 and method of the present invention, the procedure would go to FIG. 8, also a far more desirable configuration.

During further advancement of scope 14, a deep transverse colon loop is sometimes encountered. If the sigmoid looping is prevented, the deep transverse colon loop is much less of a problem. Sometimes, a longer guide 10, such as one approximately 40 to 50 cm (similar in length in to an overtube or even longer) which can be inserted to the descending colon 26 or even the transverse colon 30, can be helpful. The shorter guide 10, if used, can be removed, and exchanged for a longer guide 10. The longer length body member 44 can be made of graduated rigidity, generally becoming less rigid toward its distal end 50.

If scope 14 needs to be removed, such as when retrieving a large polyp after polypectomy, a longer guide 10 may also be helpful. The scope 14 is removed while the longer guide 10 is kept in place in the descending colon 26. When the scope 14, or another scope, is re-introduced, it can be introduced easily alongside the guide 10, back into the descending colon 26, without having to work its way through the turns of the sigmoid 24 again. In this situation, a long guide 10 with a ring member 66 at its distal end 50 can be used. The ring member 66 can be made of collapsible material, such that on reinsertion of the scope 14, the scope 14 does not have to be reinserted through the ring member 66. Once the scope 14 is in the descending colon 26, the guide 10 can be withdrawn and removed with the ring member 66 collapsed. The exchange of scopes maneuver can also be carried out easily if difficulty is encountered upstream and a hydrophilic sleeve (i.e., a sleeve member coated with a hydrophilic substance that is placed over the scope 14) is deemed desirable. The scope 14 is removed in this manner, loaded with the hydrophilic sleeve, and then reintroduced.

Occasionally, a prior art sigmoid splint/overtube is inserted over the scope 14. If it is successful, it can be very helpful in the advancement of the scope 14. However, sometimes insertion of the overtube meets resistance at the recto-sigmoid junction because there is still a bend there despite pulling the scope 14 back. At that point, the simple solution, offered with the guide 10 and method of the present invention, is to introduce the guide 10 to tilt the scope 14 in the rectum 20 to the left, and maintaining that axis as the scope 14 is pushed forward. The scope 14 from the anus 22 to descending colon 26 is kept in a relatively straight line. Buckling is avoided, and looping of the sigmoid 24 is also avoided, as shown in FIGS. 5, 6 and 8, while the scope 14 moves forward efficiently. The guide 10 and method of the present invention thus can serve the same purpose as a sigmoid splint/overtube, except it is much more easily loaded onto the scope 14, it is much easier to use (i.e., not hampered by a bent recto-sigmoid junction), and it is safer. While the purpose is similar, namely maintaining straightness from the anus 22 to the descending colon 26, the prior art overtube does not provide for or offer active tilting due to its flexibility. In addition, prior art overtubes cannot be utilized to facilitate the initial scope 14 insertion through the sigmoid 24. Further, although the guide 10 can include a ring member 66 or a tubular member 70, a totally tubular configuration is not required, as it is for the overtube.

In another method of use of the guide 10 of the present invention that is configured with a plurality of ring members 66 or one or more tube members 70 (or if tube member 70 is substantially the length of body member 44), is to first insert at least a portion of body member 44 of guide 10 into the rectum and then insert the scope 14 into engagement with ring members 66 or inside tube 70. The scope 14 and the body member 44 of guide 10 are then advanced together while the operator tilts the guide 10 in the general direction of the descending colon 26 and manipulates the scope 14 to ease the passage of insertion tube 18 through the colon 12.

It is anticipated that guide 10 of the present invention can also be utilized for medical procedures other than a colonoscopy that require the insertion of scope 14 or like medical device into the human body and where it is necessary or desirable to tilt the scope 14 so as to direct it to its target location. For instance, guide 10 is likely to be useful in a natural orifice transluminal endoscopic surgery (commonly referred to as NOTES), such as the splenectomy shown in FIG. 20. In addition to the colon, this figure shows the stomach 80, duodenum 82, spleen 84 and greater omentum 86. As shown in FIG. 20, scope 14 is inserted into the rectum 20 and then directed through an incision generally located at the recto-sigmoid junction 36 into the peritoneal cavity. Guide 10, preferably in the form of a rigid overtube, is introduced into the rectum 20 over the scope 14. Using guide 10, the operator tilts the axis of the scope 14 toward spleen 82 to perform the splenectomy or tilt to the right to perform a cholecystectomy.

While there are shown and described herein certain specific alternative forms of the invention, it will be readily apparent to those skilled in the art that the invention is not so limited, but is susceptible to various modifications and rearrangements in design and materials without departing from the spirit and scope of the invention. In particular, while the above description contains many specifics, these should not be construed as limitations on the scope of the invention, but rather as an exemplification of one or more preferred embodiments thereof. Further, it should be noted that the present invention is subject to modification with regard to assembly, materials, size, shape and use. Some of the components described herein can be made integral with each other to reduce the number of separate components. For instance, the handle 58, injection port 60, ring members 66 and/or tube 70 can be made integral with body member 44.

What is claimed is:

1. A method of using an endoscope and a guide having a rigid elongated body member with a handle at a proximal end to perform a colonoscopy in a colon, the method comprising the steps of:
    a) inserting a tip of the endoscope into the colon through the anus;
    b) advancing the endoscope in the colon;
    c) introducing a distal end of the body member into the rectum generally along the endoscope with an inner side of said body member substantially adjacent or against the endoscope;
    d) advancing the inner side of the body member along the endoscope;
    e) tilting the body member of the guide while said body member is disposed in the rectum to exert leftward force against the endoscope in the rectum so as to direct the endoscope towards the descending colon; and
    f) advancing the endoscope against the body member in the colon while the body member is tilted to perform the colonoscopy;
    wherein the advancing of step d) does not advance said body member beyond the rectum.

2. The method according to claim 1 further comprising the step of:
    g) repeating steps e) and f) as necessary upon formation of a subsequent loop in the sigmoid colon.

3. The method according to claim 1, wherein the tilting step is achieved by manipulating the handle.

4. The method according to claim 1, wherein the distal end of the body member has a curved cross-section configured to improve contact of the inner side with the endoscope.

5. The method according to claim 4, wherein the inner side of the body member is coated or lined with a liner material.

6. The method according to claim 5, wherein the liner material is coated or impregnated with a lubricant.

7. The method according to claim 1, wherein the inner side of the body member is coated or lined with a liner material.

8. The method according to claim 7, wherein the liner material is coated or impregnated with a lubricant.

9. The method of claim 1, wherein the inner side of the body member is coated or impregnated with a lubricant.

10. The method of claim 9, wherein the lubricant is a hydrophilic material.

11. The method according to claim 1, wherein the guide has an injection port generally at said proximal end of said body member on or near the handle, one or more discharge openings on the inner side of the body member and one or more channels interconnecting the injection port and the one or more discharge openings, the method further comprising the step of injecting a fluid onto the endoscope.

12. The method according to claim 1, wherein the guide further comprises a ring member integral with or attached to the body member, the ring member sized and configured to substantially encircle the endoscope.

13. The method according to claim 12, wherein the ring member comprises a slot configured to facilitate placement of the endoscope in the ring member prior to the introducing step and the method comprises the step of closing said slot prior to the introducing step.

14. The method according to claim 1, wherein the guide further comprises an elongated tube member at or near said distal end of the body member, the tube member integral with or attached to the body member.

15. The method according to claim 14, wherein the tube member extends substantially the entire length of the body member.

16. The method according to claim 15, wherein the tube member has graduated stiffness along its length, the distal end of the body member being generally more flexible than the proximal end thereof.

17. The method of claim 15, wherein the tube member is at least partially rigid.

18. A method of using an endoscope and a guide having a rigid elongated body member with a handle at a proximal end and means for engaging the endoscope at or near a distal end of the body member to perform a colonoscopy in a colon, the method comprising the steps of:
    a) inserting a tip of the endoscope into the colon through the anus;
    b) advancing the endoscope in the colon;
    c) placing the engaging means over the endoscope outside the anus; d) introducing the distal end of the body member into the rectum generally along the endoscope with the endoscope disposed in the engaging means so as to place an inner side of the body member substantially adjacent to or abutting the endoscope;

e) advancing the inner side of the body member along the endoscope;

f) manipulating the handle while said body member is disposed in the rectum to tilt the body member to exert leftward force against the endoscope in the rectum so as to direct the endoscope towards the descending colon; and g) advancing the endoscope against the body member in the colon while the body member is tilted to perform the colonoscopy;

wherein the advancing of step e) does not advance said body member beyond the rectum.

19. The method according to claim 18, wherein the engaging means comprises one or more ring members integral with or attached to the body member, each of the one or more ring members having a slot configured to receive the endoscope therein.

20. The method according to claim 19, wherein at least one of the one or more ring members is at the distal end of said body member.

21. The method according to claim 18, wherein the engaging means is a tube member integral with or attached to the body member at or near the distal end of the body member, the tube member having a slot configured to receive the endoscope therein.

22. The method according to claim 18, wherein the guide has an injection port generally at the proximal end of the body member on or near the handle, one or more discharge openings on the inner side of the body member and one or more channels interconnecting the injection port and the one or more discharge openings, the method further comprising the step of injecting a fluid onto the endoscope.

23. A method of using an endoscope and a guide having a rigid elongated body member with a handle at a proximal end and means for engaging the endoscope at or near a distal end of the body member to perform a colonoscopy in a colon, the method comprising the steps of:

a) inserting the endoscope through the engaging means;

b) moving the guide towards the proximal end of the endoscope;

c) inserting a tip of the endoscope into the colon through the anus;

d) advancing the endoscope in the colon;

e) sliding the distal end of the body member to the anus;

f) introducing the body member into the rectum generally along the endoscope with the endoscope disposed in the engaging means to place an inner side of the body member substantially adjacent to or against the endoscope;

g) advancing the inner side of the body member along the endoscope;

h) manipulating the handle while said body member is disposed in the rectum to tilt the body member to exert leftward force against the endoscope in the rectum so as to direct the endoscope towards the descending colon; and i) advancing the endoscope against the body member in the colon while the body member is tilted to perform the colonoscopy;

wherein the advancing of step g) does not advance said body member beyond the rectum.

24. The method according to claim 23, wherein the engaging means is one or more ring members integral with or attached to the body member.

25. The method according to claim 23, wherein the engaging means is a tube member integral with or attached to the body member at or near the distal end of the body member.

26. The method according to claim 23, wherein the guide has an injection port generally at the proximal end of the body member on or near the handle, the method further comprising the step of injecting a fluid onto the endoscope through the injection port.

27. A method of using an endoscope and a guide having a rigid elongated body member with a handle at a proximal end and means for engaging the endoscope at or near a distal end of the body member to perform a colonoscopy in a colon, the method comprising the steps of:

a) inserting the body member of the guide into the rectum through the anus;

b) inserting a tip of the endoscope through the anus into the colon past the body member of the guide;

c) tilting the body member against the endoscope proximal to the tip of the endoscope while said body member is disposed in the rectum to exert leftward force against the endoscope in the rectum so as to direct the endoscope towards the descending colon; and d) advancing the endoscope in the colon against an inner side of the body member while the body member is tilted to perform the colonoscopy;

wherein the inserting of step a) does not insert said body member beyond the rectum.

28. The method according to claim 27 further comprising the step of:

e) withdrawing the endoscope to reduce or straighten a loop in the sigmoid colon while maintaining the body member against the endoscope so as to generally align the rectum with the descending colon;

f) advancing the endoscope to perform the colonoscopy; and g) repeating steps e) and f) as necessary upon formation of a subsequent loop in the sigmoid colon.

29. The method according to claim 27, wherein the guide further comprises an elongated tube member extending substantially the entire length of the body member, the tube member integral with or attached to the body member.

30. The method according to claim 27, wherein the body member has graduated stiffness along its length, the distal end of the body member being generally more flexible than the proximal end thereof.

31. The method according to claim 27, wherein the colonoscope guide has an injection port generally at the proximal end of the body member on or near the handle, one or more discharge openings on the inner side of the body member and one or more channels interconnecting the injection port and the one or more discharge openings, the method further comprising the step of injecting a fluid onto the endoscope.

* * * * *